United States Patent [19]

Richalley

[11] Patent Number: 4,950,395

[45] Date of Patent: Aug. 21, 1990

[54] ARTIFICIAL KIDNEY WITH MODERATE EXCHANGE RATES

[75] Inventor: Gerard Richalley, Lyons, France

[73] Assignee: Hospal Industrie, France

[21] Appl. No.: 126,018

[22] Filed: Nov. 27, 1987

[30] Foreign Application Priority Data

Nov. 28, 1986 [FR] France ................................ 86 16867

[51] Int. Cl.$^5$ ........................ B01D 61/24; B01D 63/08
[52] U.S. Cl. ............................... 210/195.2; 210/257.2;
210/321.65; 210/321.71; 210/321.72;
210/321.75
[58] Field of Search .................... 604/4, 5; 210/195.2,
210/257.1, 257.2, 259, 321.65, 321.71, 321.72,
321.75

[56] References Cited

U.S. PATENT DOCUMENTS

| | | | |
|---|---|---|---|
| 3,506,126 | 4/1970 | Serfass et al. | 210/321.71 |
| 4,132,644 | 1/1979 | Kolberg | 210/321.65 |
| 4,545,910 | 10/1985 | Marze | 210/500.27 |
| 4,661,246 | 4/1987 | Ash | 210/321.65 |
| 4,767,526 | 8/1988 | Vantard | 210/321.65 |

FOREIGN PATENT DOCUMENTS

3426493A1  2/1985  Fed. Rep. of Germany .

OTHER PUBLICATIONS

Cobe Technical Specification for PPD 0.8, 1.3, 1.6, 1.9.

*Primary Examiner*—W. Gary Jones
*Attorney, Agent, or Firm*—Finnegan, Henderson, Farabow, Garrett & Dunner

[57] ABSTRACT

An artificial kidney capable of operating without a dialysis machine for the treatment of chronic renal failure in discontinuous sessions consisting essentially of:

a. a source of a prepackaged dialysis liquid;
b. a hemodialyzer with a high permeability membrane continuously traversed by the blood and the dialysis liquid;
c. means for collecting the used dialysis liquid and possibly the ultrafiltrate;
d. means for measuring the patient's variations in weight; and
e. possibly means for injecting a sterile and apyrogenic liquid into the extracorporeal blood circuit.

This artificial kidney is particularly intended for operating in a non-hospital environment.

19 Claims, 2 Drawing Sheets

ARTIFICIAL KIDNEY WITH MODERATE EXCHANGE RATES

The present invention relates to a new type of artificial kidney. It concerns more particularly an artificial kidney capable of operating without a dialysis machine, hence requiring only a very straightforward application of reduced material means essentially limited to an exchanger with membranes and some accessories, yet being capable of treating chronic kidney failure in discontinuous sessions.

Until now, such artificial kidneys without machines allowing the dialysis to be effected and controlled could only be used for treating acute renal conditions. In fact, these kinds of condition are generally only treated for a few weeks, the natural kidneys then progressively reassuming their function. Thus, the patients can be subjected to artificial purification means operating on a practically continuous basis with very small flows of blood and of the dialysis liquid. These continuous very small flows obviously only require a minimum of means and of supervision. The recent use of high permeability membranes has made it possible to improve the treatment quality but so far, has not modified it in its essential arrangements.

To release the patient and to treat him only during a limited weekly period, it is obviously necessary to accelerate the purification rate considerably, in particular by the combined use of high permeability membranes and high circulation rates of the blood and of the dialysis liquid in the hemodialyzer, as well as by the possible application of high pressure differences on either side of the membrane leading to ultrafiltration rates which can be very high and to a partial replacement of the ultrafiltrate (hemodiafiltration). It is clear that such severe treatments require very rigorous permanent controls of many parameters which must be completely mastered and this generally requires the use of ever more sophisticated dialysis machines which are hence expensive and difficult to operate even for staff who must be increasingly highly qualified.

This current technological trend in the means used for the treatment of chronic renal conditions leads moreover to subjecting the patient to increasing traumatisms: on the one hand, the hemolysis of the blood is not negligible and above all, the blood purification rates or the losses in weight of the patient attain such high values that they are no longer always accompanied by the corresponding transfers of liquid, within physiologically tolerable periods, between the intracellular and extracellular environments and the blood. The patient may experience from this various indispositions such as headaches, nausea, vomiting, sudden drops of blood pressure etc.

Thus to meet the increasing demands for a simple and inexpensive artificial kidney which is easy to use and non-traumatising, for the treatment of chronic renal conditions, the present invention proposes an artificial kidney which against the present day trend, essentially favours the straightforwardness and even plain simplicity of the means used with an optimum utilisation rate as regards the efficiency level of the selected and limited means available according to a combination which, thanks to reasonable discontinuous weekly sessions in particular, makes it nevertheless possible to maintain the purification rate, the patient's weight and an acid-base equilibrium in accordance with the usual standards.

Thus, one of the objects of the present invention is to propose an artificial kidney capable of treating chronic renal failure by successive discontinuous sessions which should be constituted by simple even scanty means and which are very easy to use by non-specialist medical staff.

Another object of the present invention is an artificial kidney which if necessary, practically does not require any permanent equipment, any pump, and which could, if required operate normally away from any supply network of water and/or electricty.

Another object of the present invention is, therefore, an artificial kidney which only requires an extremely low or even practically zero initial investment in permanent equipment by the user and which therefore only uses products and equipment capable of being used on a one time basis.

Another object of the present invention is nevertheless an artificial kidney essentially only requiring, if necessary, equipment which can be easily sterilized by heat in particular, so that it can, if required, be reused several times.

Another object of the present invention is an artificial kidney constituted essentially by elements capable of lending themselves to straightforward manufacture at high mass production rates, by means of robots, and therefore of a constant quality and yet obtained at very low costs.

Another object of the present invention is an artificial kidney wherewith the purifying liquid or liquids are advantageously supplied in a prepared and/or sterilized condition.

Another object of the present invention is an artificial kidney which should be particularly well adapted for dialysis outside the hospital and at home in particular, which promotes greater decentralization and also a greater availability of dialysis to the mass of the people, in particular in rural areas and more particularly in the developing countries.

Another object of the present invention is an artificial kidney which should be capable of multipurpose use, that is to say, that it should be equally well capable of treating acute or chronic conditions.

Another object of the present invention is an artificial kidney which is particularly well suited for the treatment of patients previously subjected to peritoneal dialysis but which in particular, because of the risk of peritonitis or of infection, must forego this method.

Another object of the present invention is an artificial kidney ensuring the treatment of the patient by hemodialysis and, moreover if required by hemofiltration, and simultaneously using controlled blood dialysis and ultrafiltration methods, possibly with the replacement of the ultrafiltrate by some physiological liquid.

Another object of the present invention is a non-traumatising artificial kidney in particular from the cardiovascular point of view because it only uses moderate flows of blood.

Another object of the present invention is to combine the conditions for a maximum efficiency for the exchanges through the membrane, allowing in particular the best possible use to be made of each liter of dialysis liquid and of blood and each square centimeter of the membrane.

Other objects of the present invention will become clear in the course of the following description.

There has now been discovered an artificial kidney capable of ensuring the treatment of a patient's chronic renal failure by discontinuous sessions over a weekly total of less than or equal to about 24 hours, consisting essentially of:

(a) a source of dialysis liquid, (b) means for collecting the said used dialysis liquid, as well as the ultrafiltrate if applicable.

(c) a high permeability membrane of the hemodialyzer type comprising two compartments separated by a membrane, the first compartment adapted to be traversed by the blood and connected to the patient's arterio-venous system by an extracorporeal blood circuit of the type known per se, and means for preventing the coagulation of blood in the said circuit, the second compartment being adapted to be continuously traversed by said dialysis liquid and collect, if applicable, the ultrafiltrate and being connected on one end, via a first conduit to a source of the fresh dialysis liquid and on the other end, via a second conduit to the said means for collecting the said used dialysis liquid and if applicable, said ultrafiltrate by means of lines allowing a flow rate comprised between 50 and 200 ml/minute, the said exchanger simultaneously offering in these conditions:

a dialysis exceeding or equal to 40 ml/minute for the clearance of urea, and an ultrafiltration capacity exceeding or equal to 8 ml/h/mmHg.

(d) means for continuously flowing sterile and apyrogenic dialysis liquid using the force of gravity through said second compartment at a rate of between 50 to 200 ml/min.

(e) means for continuously flowing blood through said first compartment during said treatment session using the pressure of the patient's arterio-venous system.

(f) means for continuously maintaining a higher pressure in said first compartment than in said second compartment.

(g) means for measuring the variation of the patient's weight due to the balance of the quantities of the liquids injected and/or withdrawn during the said treatment.

The preparation of dialysis liquid from tap water and a bulk concentrate does not form part of the present invention. In fact in the environment outside the hospital and in the absence of a dialysis machine, the user must have a source of dialysis liquid supplied in a preprepared form.

Thus the user can receive containers containing volumes of water duly determined in quantity and quality. He can receive at the same time corresponding doses of concentrate and of anappropriate composition such as prepared for conventional dialysis, depending on the type of patient to be treated and all he will have to do is to mix them just before the treatment.

Preferentially the user can use containers or leak-proof reservoirs made of a flexible plastic material containing determined volumes of previously prepared dialysis liquid. He will for example be able to use several reservoirs to attain the qualities and quantities of dialysis liquid necessary for one dialysis session for a given patient.

Advantageously, the dialysis liquid thus stored can be delivered in a sterile and apyrogenic condition allowing the user to effect the following operations with the same liquid, such as:

preliminary rinsing of the hemodialyzer
dialysis of the blood
injection of liquid into the blood to offset the whole or part of the ultrafiltrate withdrawn from the patient, or even to complement the patient's nutrition.

restoring the blood to the patient at the end of the session.

The volume of dialysis liquid necessary for one hemodialysis session is generally less than or equal to 60 liters and preferably less than or equal to 40 liters. 25 liters can be adequate for one dialysis session.

The artificial kidney according to the invention comprises essentially, apart from the said source of dialysis liquid, a membrane exchanger separated into two compartments by a semipermeable membrane of the high permeability type. The first compartment traversed by the blood, is connected to the patient's arterio-venous system by an extracorporeal blood circuit known per se, advantageously without a blood circulating pump and provided with conventional means for avoiding clotting of the blood.

The second compartment is traversed by the dialysis liquid. It is, therefore, connected by appopriate conduits to the source of the dialysis liquid on the one hand and on the other hand, to means making it possible to collect and to measure the amount (weight or volume) of the used dialysis liquid, as well as, if applicable, the amount of the ultrafiltrate which would have traversed the membrane.

The membrane exchanger is advantageously constituted by a hemodialyzer of a type known per se. Although a hemodialyzer with a tubular flattened membrane, rolled in spirals or a bundle of hollow fibres is quite suitable, one nevertheless prefers the hemodialyzer of the flat membrane type supported for example, by ribbed inserts. Generally the effective area of the membrane is comprised between 0.3 and 1.5 $m^2$ and preferably between 0.4 and 1.2 $m^2$. Membranes with an effective area comprised between 0.5 to 1 $m^2$ or equal to these values are entirely suitable.

The blood and the dialysis liquid can circulate in contraflow, in concurrent flows or in cross flow in the hemodialyzer. Advantageously a concurrent circulation in an exchanger with flat membranes makes it possible to obtain a minimum rate of ultrafiltration which is practically zero.

The membrane allowing the dialysis and ultrafiltration of the blood is of the high permeability type. Preferentially, this is a membrane such as claimed in the U.S. Pat. No. 4,545,910 or the European Patent No. 100,285.

A dialysis liquid circuit connects the dialysis liquid source to means for collecting the used dialysis liquid through the second compartment of the hemodialyzer, to means for collecting the used dialysis liquid and the ultra filtrate, this circuit is provided with means allowing the flow, preferably by gravity, of a throughout of dialysis liquid generally comprised between 45 and 500 ml/minute and preferably between 50 and 200 ml/minute. This rate of flow can be selected for example, by means of a clamp with adjustable shut off stages obturating a conduit with elastic walls made for example, of a transparent polyvinyl chloride, to a greater or lesser extent. This throughput is advantageously measured with a flow meter giving an accuracy of at least 5%. As flow meter, one can use very simple disposable devices, for example without any moving parts such as described in the German Patent No. 2,504,402.

The blood generally flows at a flow rate comprised between 80 and 200 ml/minute and preferably between 100 and 150 ml/minute, a pump being most frequently used only to guard against a possible failure of the natural flow. In these conditions, it will be observed that the exchanger can offer a dialysis capacity exceeding or equal to 40 ml/minute and preferably exceeding or equal to 50 ml/minute for the clearance of urea.

Similarly, it offers an ultrafiltration capacity generally exceeding or equal to 8 ml/h/mmHg and preferably exceeding or equal to 10 ml/h/mmHg.

It will then be observed that the weekly duration of the treatment of chronic renal conditions can be less than or equal to 24 hours and preferably less than or equal to 18 h. That is to say, for example, three sessions in the week of 8 h each, or preferably 6 h whilst respecting the usual standards of purification, of weight maintenance and of the acid-base equilibrium.

The measurement of the amount (weight or volume) of the liquid collected either at the end of the session or preferably during the session makes it possible to ascertain, by comparison with the amount (weight or volume) of the fresh dialysis liquid used, the amount of the ultrafiltrate possibly withdrawn from the patient, and hence the variation of his weight, and to control this parameter either, preferably during one session or from one session to another.

Possibly, the used dialysis liquid may be collected at the outlet of the exchanger with the ultrafiltrate if applicable in a container insulated from the atmosphere by a sterile filter. The liquid thus collected can be purified at least partly by passing through active charcoal so as to be reused later after being reconditioned or preferably be immediately recycled. Thus the supplies of fresh dialysis liquid can be substantially reduced. As a variant, the liquid leaving the exchanger can be directly recycled by being pumped into the latter after passing through a cartridge of active charcoal or not.

It has been found that with the means, and in the conditions set out above it was possible, operating in the ambit of treatment of chronic renal conditions, to obtain in particular purification rates that were entirely satisfactory for the patients and conformed to the usual standards applied.

Thus according to the work of the "National Cooperative Dialysis Study" (NCDS) published in particular by Gotch and Sargent in Kidney International, vol. 28 (1985), pages 526-534 (cf FIG. 7 and corresponding comments), the table below indicates the preferably minimal urea clearances (in ml/minute) which must be obtained from a hemodialyzer provided with conventional cellulose membranes to guarantee adequate purification according to the weight and the catabolism rate of proteins of each patient, for example for weekly sessions of 6 hours every other day with a loss in weight estimated at 4% of the total weight.

| Catabolism rate of the proteins gr/Kg/day | Weight 45 Kg | 50 | 55 | 60 | 65 | 70 |
| --- | --- | --- | --- | --- | --- | --- |
| <0,9 | 58 | 65 | 71 | 78 | 84 | 91 |
| 0,95 | 58 | 65 | 72 | 78 | 85 | 91 |
| 1,00 | 59 | 66 | 72 | 79 | 85 | 92 |
| 1,05 | 62 | 69 | 76 | 82 | 89 | 96 |
| 1,10 | 65 | 72 | 79 | 86 | 93 | 100 |

It will be observed that the values are remarkably low and it has been found that they can be obtained with a very wide safety margin for example with a hemodialyzer for SCU-CAVE of an effective surface area of 0.7 $m^2$ of a membrane made of copolymers of acrylonitrile AN 69, marketed by the HOSPAL Company.

With the artificial kidney according to the invention, the urea clearance is, thanks to the relatively low flow rates of the dialysis liquid, practically equal to the corresponding flow rate of the dialysis liquid expressed in ml/minute. It will be found that these values of the clearance, and hence of the flow rate of the dialysis liquid fall within the preferential range indicated above (50-200 ml/minute).

An understanding of the present invention will be facilitated by the attached figures which schematically illustrate various modes of embodiment of the artificial kidney according to the present invention by way of examples and without any determined scale.

For greater clarity, the similar elements represented in the various figures bear the same reference numerals.

Figure 1:
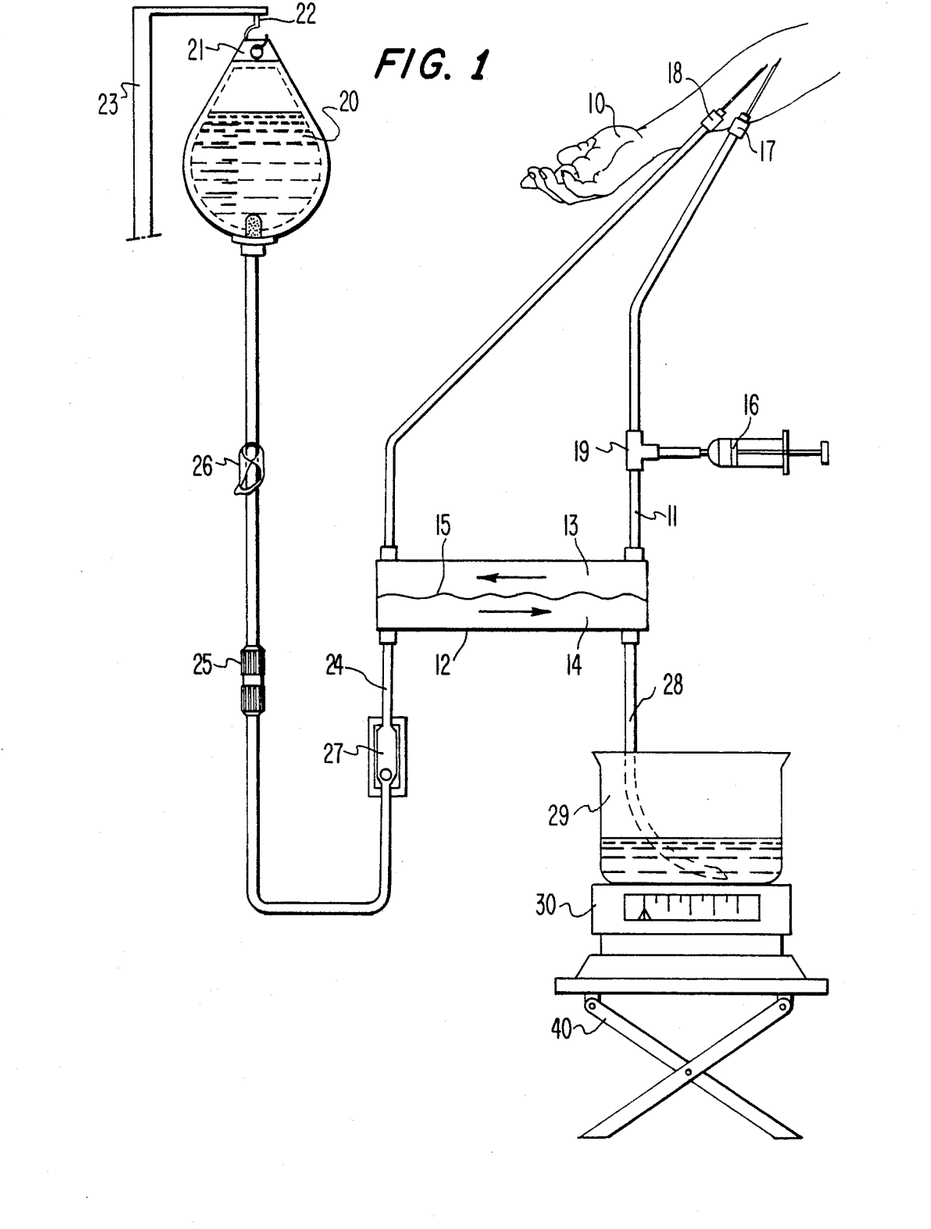
FIG. 1 represents a first preferential and very simple mode of embodiment of the artificial kidney according to the invention permitting treatment by hemodialysis.

Referring to FIG. 1 it will be seen that the vascular system of the patient (10) is connected for example, to a fistula, nozzle or arterio-venous shunt (17, 18) to the ends of an extracorporeal blood circuit (11) connected to a hemodialyzer (12). The latter is schematically divided into two compartments (13) and (14) by semipermeable membrane (15). The compartment (13) is traversed by the blood and the compartment (14) is traversed in contra-flow by the dialysis liquid. A syringe (16) whose end is connected by a connector (19) to the arterial side of the extracorporeal blood circuit (11) allows the necessary doses of an anti-coagulent such as heparin to be injected.

Some fresh dialysis liquid having the same composition as dialysis liquid intended for conventional dialysis has been previously prepared and stored, for example in a plurality of reservoirs such as (20), made of a flexible plastic material with a capacity generally comprised between 1 and 12 liters and preferably between 2 and 8 liters. Reservoirs of a 5 liter capacity are very suitable. Advantageously, they are made of transparent PVC, graduated in liters and comprise at their upper end an opening (21) allowing them to be suspended by a hook (22) on a gallows (23). They can be connected to the compartment (14) of the hemodialyzer (12) in parallel and be placed into use successively and/or simultaneously. Having previously been heated, for example in a water bath up to approximately 40° C., they keep the dialysis liquid at a sufficient temperature during use so as not to give the patient a sensation of cold.

A line (24) made of transparent polyvinyl chloride connects the inlet opening of the compartment (14) of the hemodialyzer (12) to the reservoir (20) by way of a sterile connector device (25) known per se. A clamp (26), also of a type known per se makes it possible either to obturate the line (24), or to adjust the flow rate of the dialysis liquid to the desired values which can be verified by means of the flow meter (27).

A reservoir (29) open to the atmosphere, having preferably a slightly greater capacity than that of the reservoir (20) is connected by a line (28) to the outlet opening of the compartment (14) of the hemodialyzer (12). The line (28) dips as far as the bottom of the reservoir (29) which is disposed on a weighing machine (30) which is itself placed above the ground.

The operation of the artificial kidney represented in FIG. 1 is as follows. Having set up the various connections, the blood circuit is treated with heparin. The blood circulation is established in the extracorporeal blood circuit (17, 11, 13, 18) where it takes place naturally under the effect of the patient's heart beat by way of the arterio-venous pressure difference, between the points of access to the vessels. In the absence of a pump assisting the natural blood circulation, the extracorporeal circuit can be relatively short and afford small drops in pressure permitting blood flow rates generally comprised between 80 and 200 ml/minute.

Advantageously, the dialysis liquid contained in the reservoir (20) is first brought to a temperature of the order of 40° C. and this liquid remains at sufficient temperatures during the session so that the patient should not experience any sensation of cold.

The clamp (26) is then opened and its position is then adjusted, so that for example, a total volume of 25 liters of dialysis liquid should flow out during the period of six hours provided for the session, which corresponds to a flow rate of approximately 70 ml/minute, indicated by the flowmeter (27). The dialysis liquid then traverses the compartment (14) of the hemodialyzer, then, having absorbed the impurities which have diffused from the blood through the membrane (15), it flows out through the line (28) into the reservoir (29).

Generally the blood is in the hemodialyzer (12) at a pressure slightlly exceeding that of the dialysis liquid. This leads to a transfer by ultrafiltration of water and of various impurities of a molecular weight which generally can amount to as much as 40,000 Daltons, from the blood into the dialysis liquid. The ultrafiltrate thus obtained flows out with the used dialysis liquid into the reservoir (29).

It is easy to regulate the flow of the ultrafiltrate by any known means for example, to increase it, either by reducing the pressure in the compartment (13) or by raising the pressure in the compartment (14) or both or vice versa. It is thus that the flow of the ultrafiltrate can be increased, for example by lowering the reservoir (29) in relation to the hemodialyzer, that is to say, by lowering the support (40) and by constricting the extracorporeal blood circuit a little at the outlet of the hemodialyzer by a clamp (not shown).

Figure 2:
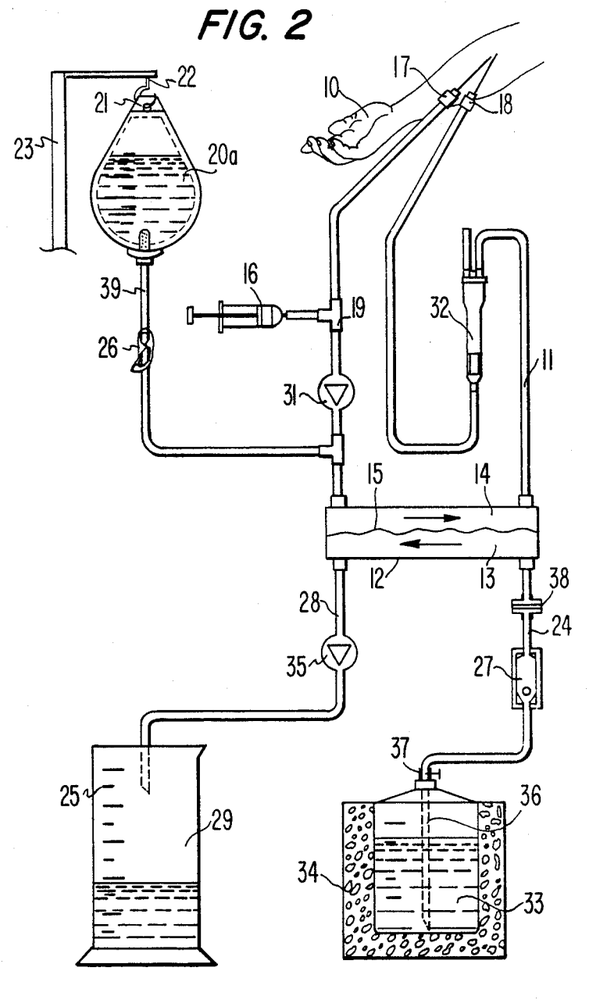
FIG. 2 represents a second mode of embodiment of the artificial kidney according to the invention permitting treatment by hemodialysis and by hemofiltration.

FIG. 2 represents a second mode of embodiment of the artificial kidney according to the invention, permitting treatment by hemodialysis and by hemofiltration (ultrafiltration accompanied by the injection into the blood of a volume of a physiological liquid, partly or wholly offsetting, or even somewhat exceeding the volume of the ultrafiltrate withdrawn).

The extracorporeal blood circuit here comprises a circulating pump (31) of the peristaltic type. The extracorporeal blood circuit can also include a bubble clearing device (32) of any kind known per se. It can, moreover, comprise an active charcoal cartridge (not shown) disposed in series with the hemodialyzer which makes it possible to increase the purification efficiency without requiring more dialysis liquid.

A 30 liter capacity container (33) made of polyethylene, advantageously translucent and graduated in liters, contains dialysis liquid of the appropriate composition for conventional dialysis. This container (33) is placed into a thermally insulated enclosure (34) made of expanded polystyrene. A self priming pump (35), for example of the peristaltic type, is disposed on the conduit (28) downstream from the hemodialyzer (12) and for displacing the dialysis liquid by drawing it from the container (33) and delivering it into the reservoir (29) made of a translucent or transparent material provided with gradations 25. The dialysis liquid, previously heated for example in a water bath, maintains a sufficient temperature during the period of the session. It is drawn from the bottom of the container (33) by a dip tube (36); it traverses the shut-off valve (37) of the container in its open position, then if applicable, means for the continuous sterilisation of the dialysis liquid constituted for example by a filter (38) of a type known per se. The function of the pump (35) is essentially to make it possible to obtain the desired ranges of the flow rates of the liquid, even when, taking the weight and the relative bulk of the container (33) and of its shell (34) into account, it would scarcely be practical to rely on gravity. The pump (35) moreover makes it possible in conjunction with a clamp (not represented) placed on the line (24) upstream from the hemodialyzer (12), to obtain the low pressure in the compartment (13) of the hemodialyzer which is necessary for obtaining the desired quantities of ultrafiltrate, even if these are large, as in the case of hemofiltration.

The respective gradations of the container (33) and of the reservoir (29) permit an assessment at any time of the volume of ultrafiltrate collected by comparing the difference.

A reservoir (20a), suspended on the gallows (23) is connected by the conduit (39) to the extracorporeal blood circuit (11) at the hemodialyzer inlet. The opening and adjustment of the opening of the clamp (26) make it possible to introduce the desired quantities of a sterile and apyrogenic physiological liquid contained in this reservoir, into this extracorporeal blood circuit (11) by gravity. This liquid can thus be used for effecting in a way known per se, operations such as:

preliminary rinsing of the hemodialyzer and/or:
the initial filling of the extracorporeal blood circuit,
the injection of liquid into the blood for compensating the whole or part of the ultrafiltrate withdrawn from the patient or if necessary, for feeding the latter and-/or detoxifying him.
restoring the blood to the patient at the end of the session.

The following example shows an application of the artificial kidney according to the invention.

A 56 year old patient has been treated for renal insufficiency which was at first acute, then chronic. A postoperative weakness has caused him to be directed on to a non-traumatising artificial kidney.

This kidney essentially comprises:

during the first month of treatment, a hemodialyzer with hollow fibres made of acrylonitrile copolymers of the FILTRAL TM type, with an effective surface area of 0.56 m$^2$, marketed by the HOSPAL Company. This hemodialyzer is connected to an extracorporeal blood circuit without a circulating pump, this circuit being itself connected to the patient by a tibial shunt.

then, after 1.5 months, a hemodialyzer with flat membranes of the BIOSPAL TM SCU-CAVE with an effective surface area of 0.5 m$^2$, marketed by the HOSPAL Company. This hemodialyzer is connected to the patient by an arterio-veinous fistula and to a extracorporeal blood circuit comprising a blood circulating pump maintaining a blood flow rate of 150 ml/minute.

a dialysis liquid circuit which delivers by means of a pump, 20 liters (four bags of five liters) of sterile liquid in six hours. The sessions taking place every other day, the weekly consumption of the dialysis liquid is thus limited to seventy liters.

The dialysis liquid has the following composition in milliequivalents per liter:

| sodium | 139.5 | magnesium | 1.5 |
|--------|-------|-----------|-----|
| potassium | 1 | chloride | 100.25 |
| calcium | 3.75 | lactate | 45.5 |

According to the table given above, it will be found that to treat a patient weighing 45 kg and having a protein catabolism rate of 0.99 gr/Kg/day, in sessions totalling 21 hours per week (six hours every other day), a hemodialyzer is required providing a total preferably minimum urea clearance of 59 ml/mn.

In these conditions, it will be found that the stabilised urea rate established in this patient is:
before treatment at: 1.59±0.22 gr/liter
after treatment at: 0.91±0.13 gr/liter
which places this treatment into the zone termed "adequate dialysis" of FIG. 7 of the above mentioned article by GOTCH and SARGENT, the predialytic urea rate of 1.59 corresponding on the y axis to a value of 74.2 milligr/deciliter (B.U.N.=blood urea nitrogen).

It will moreover be found that the average urea extraction per dialysis session was equal to 24.2±4.3 gr.

The delivery of the fresh dialysis liquid was, on average 55.55 ml/mn.

The average delivery collected at the outlet of the dialyzer was 59.88±8.9 ml/mn. Hence by comparing the difference, the average delivery of ultrafiltrate is 4.33 ml/mn. that is to say, an amount of 3.5% in relation to the patient's weight.

Moreover, the total urea extraction, thus taking the ultrafiltrate into account, calculated on the basis of the formula $$K_T = \frac{C_D \times Q_D}{C_S}$$

where:
$C_D$: is the urea concentration of the dialysis liquid at the outlet
$Q_D$: is the delivery of the dialysis liquid at the outlet of the dialyzer
$C_S$: is the average urea concentration in the blood.
gives $K_T$=53.8 ml/minute.

Finally, it will be found that this value, although a little lower than the 59 ml/minute shown in the above table is nevertheless satisfactory, because with the high permeability membranes used, the purification of molecules with a higher molecular weight than that of urea is considerably better than with the conventional cellulose membranes.

It is thought that the quality of these results could be due to the fact that the artificial kidney according to the invention requires the blood and the dialysis liquid to circulate continuously on each side of the membrane at moderate rates and for periods which are found to correspond to values near the optimum as far as the exchange efficiency through the membrane is concerned. The conditions of implementation and the means which have been defined within the scope of the present invention make it possible to benefit from the main factor of the purification potential afforded at one and the same time by each $cm^2$ of the membrane and by each $cm^3$ of dialysis liquid, the latter emerging from the exchanger with a rate of impurities which is very close to that of the blood on entry.

Thus the kidney according to the invention would make it possible to derive a better advantage from the potential offered by the high permeability membrane than the kidneys treating acute renal failure by continuous arterio-venous dialysis because the latter only make use of dialysis liquid rates of the order of 15 ml/minute which would be too slow in this connection.

On the contrary, for the treatment of chronic renal failure, the current artificial kidneys use increasingly high rates for the blood and dialysis liquid by means of multiple pumps which on the one hand is not done without hemolysis of the blood, and on the other hand, would not make it possible to derive the best advantage from each liter of dialysis liquid, since the latter does not have time to absorb the maximum of impurities.

It will thus be observed that in accordance with the present invention, one can treat chronic renal conditions without the use of a dialysis machine according to the usual standards of the purification rates and of the weight balance and the acid base equilibrium within the scope of discontinuous sessions of a duration over the week which are entirely acceptable.

It will be observed that the means used are mostly extremely straightforward and economical and even deliberately simple:
graduated reservoirs, flexible conduits with standard devices for their connection, their obturation being adjustable.
means for heating or for maintaining the temperature,
means for measuring the flow rates, weights and volumes.

On the other hand, certain means are on the contrary, highly developed products: high permeability membranes, hemodialyzers, sterile and apyrogenic liquids. They can then be supplied prepackaged and ready for use.

All these means thus lend themselves to a simple, rapid, reliable application, even by non-specialist staff and even by the patient himself. This artificial kidney can function even if neither water nor electricity are available locally. The cost of the initial investment is obviously minimal. Certain means may be optionally used on a one time basis or be sterilised and reused if desired.

It will be observed that since the flow rate of the dialysis liquid in the dialyzer is rather slow, it has time to absorb the maximum of impurities and the volume of the dialysis liquid necessary for one session is therefore reduced, which permits more carefully prepared packaging (at the same cost), sterile and apyrogenic for example which has the advantage of allowing a multipurpose use of this liquid in the best possible conditions of hygiene and reliability.

This artificial kindney is equally well suited to the treatment of acute or chronic conditions. Although it can function without difficulty in a hospital environment, it is clear that it will be particularly useful remote from dialysis centres which are already well equipped, either at home or in treatment centres in a rural environment or yet again in the developing countries.

Being simple, flexible in use, applying the techniques of hemodialysis, as required, either on their own or in conjunction with hemofiltration with injection of a physiological liquid compensating the whole or part of the untrafiltrate withdrawn. It can also advantageously treat patients treated so far by peritoneal dialysis, but being obliged to change the treatment method in the face of the risks of peritonitis or of infection.

It is within the expert's grasp to combine the various means described in the present application with each other, or to replace them by some equivalent devices. The artificial kidney described above can moreover be obviously the object of many other variants of the embodiment within the expert's reach without thereby departing from the scope of the present invention.

What is claimed is:

1. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50-200 ml/minute;

means for continuously flowing blood through said first compartment during said treatment session using the pressure of the patient's arterio-venous system;

means for continuously maintaining a higher pressure in said first compartment than in said second compartment during said treatment session; and means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg.

2. An artificial kidney according to claim 1, wherein said source of the dialysis liquid is constituted by fresh dialysis liquid prepackaged in at least one reservoir whose total capacity for one session is less than or equal to 60 liters.

3. An artificial kidney according to claim 1, wherein said exchanger is of the flat membrane type.

4. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force or gravity through said second compartment at a rate of between about 50-200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg;

wherein said source of the dialysis liquid is constituted by fresh dialysis liquid prepackaged in at least one reservoir whose total capacity for one session is less than or equal to 60 liters; and including means for sterilizing said dialysis liquid before it enters into said exchanger.

5. An artificial kindney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said for collecting said used dialysis liquid and any ultrafiltrate;

means for continuously flowing sterile and apyrogenic dialysis liquid using the force of gravity through said second compartment at a rate of between about 50-200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg; and including means for purifying the liquid collected at the outlet of said exchanger at least partly, so that it can be reused.

6. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50–200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg; and including a reservoir filled with a physiological, sterile and apyrogenic liquid and means for connecting said reservoir to said extracorporeal blood circuit to allow at least oen of the following operations to be performed: preliminarily rinsing said exchanger, initially filling said extracorporeal blood circuit, compensating at least partly the ultrafiltrate withdrawn from the patient, complementarily feeding the patient, detoxification of the patient, or restoring the blood to the patient at the end of the session.

7. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50–200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg; and including means for maintaining the dialysis liquid at temperatures approximating that of the patient's blood.

8. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50–200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg; and wherein the effective surface area fo said membrane of said exchanger is between 0.3 and 1.5 m$^2$.

9. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50–200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg; and including means for allowing the blood to flow into said exchanger at a flow rate between 80 and 200 ml/minute.

10. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeabilty membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50–200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg; and including means for regulating the flow rate of the fresh dialysis liquid traversing said exchanger.

11. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50–200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg; and including means for measuring the flow rate of the dialysis liquid traversing said exchanger.

12. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeabilty membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50–200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg; and including means for regulating the flow of any ultrafiltrate extracted from the blood through said membrane of said exchanger.

13. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50–200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg; and including means for recirculating the dialysis liquid in said exchanger.

14. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50–200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg;

wherein said exchanger is of the flat membrane type; and, including means for allowing a concurrent circulation of the blood and dialysis liquid in said exchanger.

15. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50-200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg; and including at least one absorption cartridge containing active charcoal disposed in said extracorporeal blood circuit in series with said exchanger.

16. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50-200 ml/min;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

wherein said membrane exchanger simultaneously provides a dialysis capacity exceeding or equal to about 40 ml/minute for the clearance of urea and an ultrafiltration capacity exceeding or equal to about 8 ml/h/mmHg;

means for recirculating the dialysis liquid in said exchanger; and including means for accomplishing treatment by hemofiltration wherein quantities of a sterile and apyrogenic liquid are adapted to be injected into the blood in amounts equivalent to the quantities of liquid withdrawn from the blood by hemofiltration less a desired variation of the patient's weight.

17. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50-200 ml/minute;

means for continuously flowing blood at a natural flow rate through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment; and pump means for flowing blood through said first compartment when blood flow through said first compartment falls below said natural flow rate;

wherein said membrane exchanger simultaneously provides a dialysis capacity exceeding or equal to about 40 ml/minute for the clearance of urea and a ultrafiltration capacity exceeding or equal to about 8 ml/h/mmHg.

18. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and at the other end via a second conduit to said means for collecting said used dialysis liquid and any ultrafiltrate;

means for continuously flowing sterile and apyrogenic dialysis liquid using the force of gravity through said second compartment at a rate of between about 50–200 ml/minute;

means for continuously flowing blood through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment; and pump means for flowing said dialysis liquid through said second compartment when gravity cannot be relied upon to provide a necessary flow rate;

wherein said membrane exchanger simulataneously provides a dialysis capacity exceeding or equal to about 40 ml/minute for the clearance or urea and an ultrafiltration capacity exceeding or equal to about 8 ml/h/mmHg.

19. An artificial kidney capable of ensuring the treatment of a patient's chronic renal failures by discontinuous sessions of a weekly total of less than or equal to about 24 hours, consisting essentially of:

a source of dialysis liquid;

means for collecting the used dialysis liquid and ultrafiltrate;

a high permeability membrane exchanger of the hemodialyzer type comprising two compartments separated by a membrane, the first compartment adapted to be traversed by the blood and connected to the arterio-venous system of the patient by an extracorporeal blood circuit, and means for preventing the clotting of blood in said circuit, the second compartment being adapted to be continuously traversed by said dialysis liquid, to collect any ultrafiltrate, and to be connected at one end via a first conduit to said dialysis liquid source and the other end via a second conduit to said means for collecting said used dialysis liquid and any ultrafiltrate;

means for continuously flowing sterile and apyrogenic dialysis liquid using the force of gravity through said second compartment at a rate of between about 50–200 ml/minute;

means for continuously flowing blood at a natural flow rate through said first compartment during said treatment session using the pressure of the patient's arterio-venous system;

means for continuously maintaining a higher pressure in said first compartment than in said second compartment during said treatment session;

means for measuring the variation of the weight of the patient due to the balance of the quantities of the liquids injected and withdrawn during said treatment;

first pump means for flowing blood through said first compartment when blood flow through said first compartment falls below said natural flow rate; and second pump means for flowing said dialysis liquid through said second compartment when gravity cannot be relied upon to provide a necessary flow rate;

wherein said membrane exchanger simultaneously provides a dialysis capacity exceeding or equal to about 40 ml/minute for the clearance of urea and an ultrafiltration capacity exceeding or equal to about 8 ml/h/mmHg.

* * * * *